United States Patent [19]
Lee

[11] Patent Number: 5,203,777
[45] Date of Patent: Apr. 20, 1993

[54] RADIOPAQUE MARKER SYSTEM FOR A TUBULAR DEVICE

[76] Inventor: Peter Y. Lee, 5118 Beechgrove NE., Canton, Ohio 44705

[21] Appl. No.: 853,921

[22] Filed: Mar. 19, 1992

[51] Int. Cl.⁵ .............................................. A61M 25/00
[52] U.S. Cl. ................................. 604/280; 128/658
[58] Field of Search ............... 604/280, 281, 282, 117, 604/264; 128/657, 658

[56] References Cited

U.S. PATENT DOCUMENTS

| | | |
|---|---|---|
| 3,605,750 | 9/1971 | Sheridan et al. ............ 128/658 |
| 3,885,561 | 5/1975 | Cami ........................... 604/280 |
| 4,027,659 | 6/1977 | Slingluff . |
| 4,041,931 | 8/1977 | Elliott et al. . |
| 4,279,252 | 7/1981 | Martin . |
| 4,419,095 | 12/1983 | Nebergall et al. . |
| 4,447,239 | 5/1984 | Krutten ....................... 604/282 |
| 4,577,637 | 3/1986 | Mueller, Jr. . |
| 4,671,291 | 6/1987 | Wilson . |
| 4,693,237 | 9/1987 | Hoffman et al. . |
| 4,796,637 | 1/1989 | Mascuch et al. . |
| 4,838,879 | 6/1989 | Tanabe et al. . |
| 4,938,220 | 7/1990 | Mueller, Jr. . |

Primary Examiner—John D. Yasko
Attorney, Agent, or Firm—Fay, Sharpe, Beall, Fagan, Minnich & McKee

[57] ABSTRACT

A radiopaque marking system for a device meant to be inserted into a body, such as a medical device inserted into a human body, and imaged with an x-ray source includes a tube having a distal end and an outer periphery which can be divided into four quadrants. A first radiopaque marker section is located only in a first quadrant of the body adjacent the distal end thereof. A second radiopaque marker section is located only in a second quadrant of the body adjacent the distal end portion. If desired, the two marker sections can contact each other along at least one corner of the two sections.

24 Claims, 4 Drawing Sheets

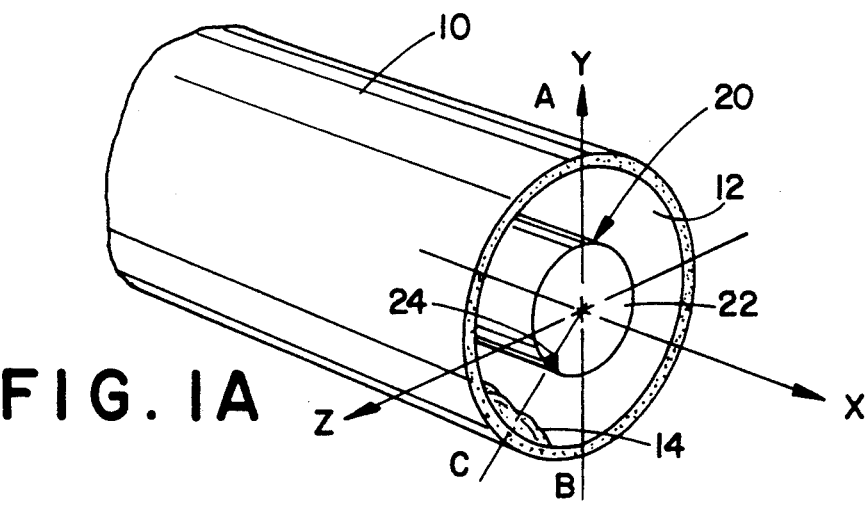
FIG. IA
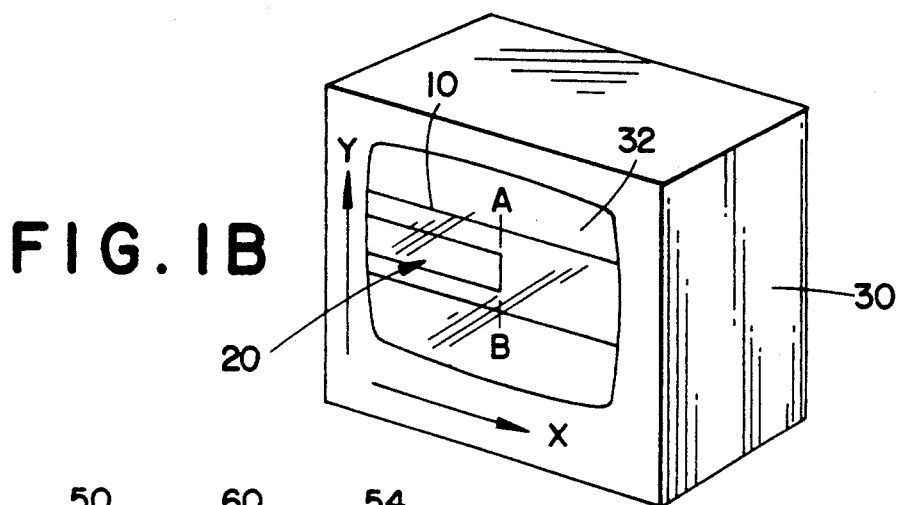
FIG. IB
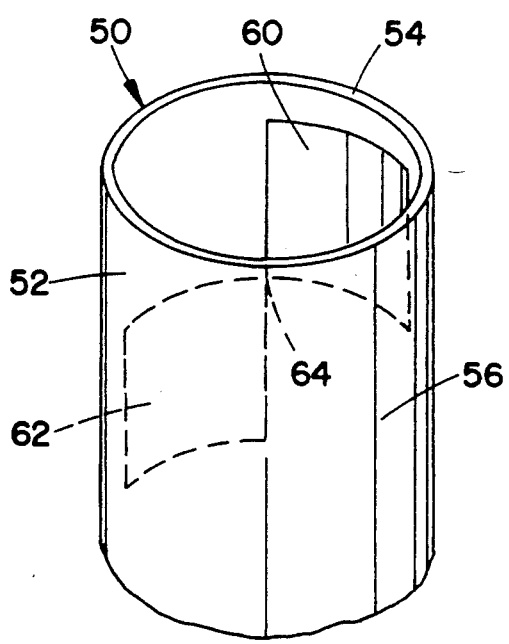
FIG. 2
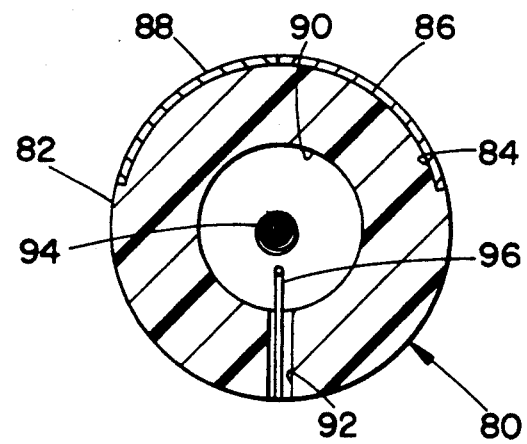
FIG. 3

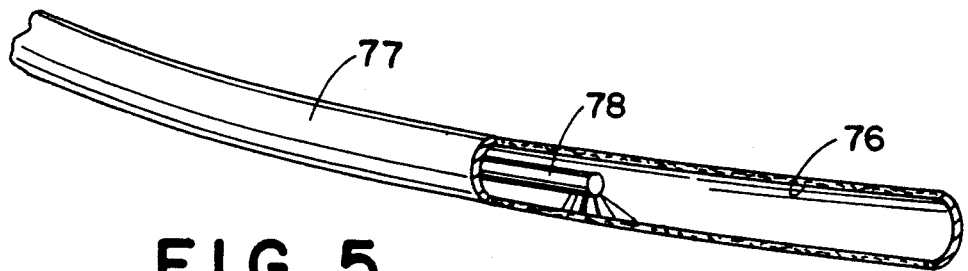
FIG. 5
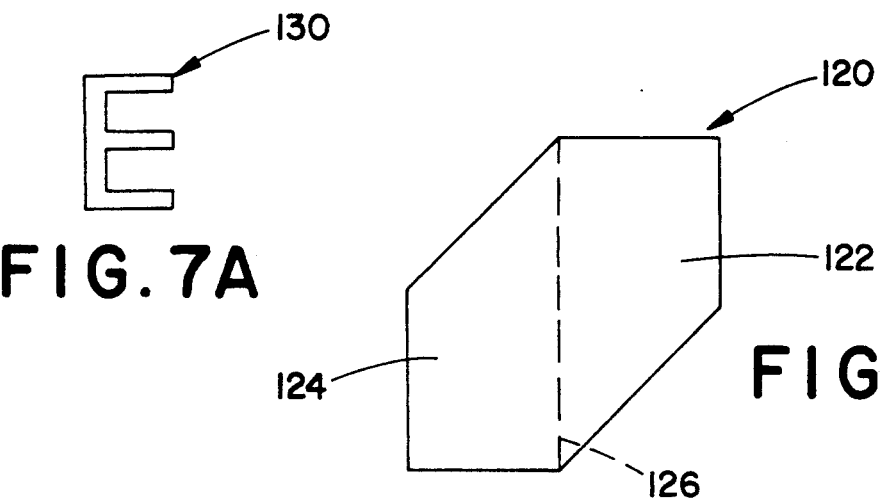
FIG. 7A
FIG. 6B
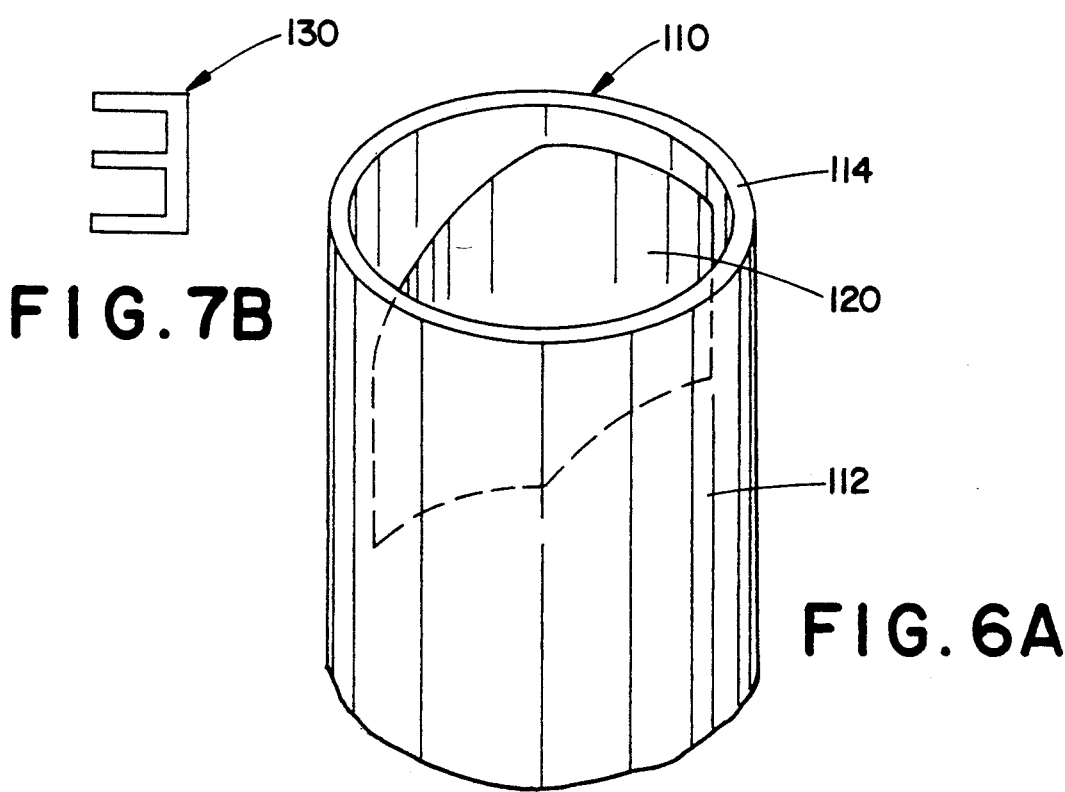
FIG. 7B
FIG. 6A

RADIOPAQUE MARKER SYSTEM FOR A TUBULAR DEVICE

BACKGROUND OF THE INVENTION

This invention relates generally to a tubular device meant to be inserted into an object and imaged with an X-ray source. More particularly, the present invention relates to such a device having an X-ray contrast medium function.

The present invention is especially suited for use in a medical environment such as use in a catheter, an angioscope, a directional atherectomy device, a cannula or the like. It should, however, be appreciated that the subject invention is capable of broader applications and could be used, e.g. in an industrial setting or in any other environment where a tubular device is inserted into an object and needs to be localized by means of X-ray radiation or the like.

Medical radiography is performed using essentially a point source of X-rays whose beams expand, pass through living tissue being investigated and expose an X-ray sensitive emulsion coated on film or expose a fluorescent screen in accordance with the attenuation intensity of the X-rays. A fluoroscope is an instrument for visual observation of the deep structures of a body by means of X-ray. A patient is put into a position such that the portion of the body to be viewed is placed between an X-ray tube and a fluorescent screen. X-rays from the tube pass through the body and project the bones and organs as shadowy images on the screen. A radiopaque medium aids in this process of examination of the body, which is called fluoroscopy.

Various types of catheters such as an angiographic catheter, a urethral catheter, a bronchographic tube or a thoracic catheter have been conventionally used in medicine for indwelling in body cavities. Often, an X-ray contrast medium is mixed partially or entirely in these catheters or employed to circumferentially form a ring mark on the outer surface of the catheters. A doctor inserts the catheter having an X-ray contrast medium into a body cavity while observing an X-ray fluoroscopic image. Fluoroscopically visible tip markers on such catheters permit the longitudinal positioning of the catheters to be monitored as they are inserted into the vascular system of the patient. Such markers typically consist of one or more bands of radiopaque material mounted on the distal end portion of the catheter.

It is also a common practice in the medical field for a physician to insert a cannula through a natural opening in a patient's body, such as the nasal or oral opening or through an incised opening and to advance the cannula to a particular location within the body. In order to properly place these cannulas, and especially their distal tips, within the body so that they will accomplish their intended purpose without injuring the patient's internal tissue, a physician or radiologist typically uses an X-ray photograph or a fluoroscope to examine the location of the cannula within the body. Often a fluoroscope is used to visually monitor the location of the cannula as it is being inserted. Therefore, it is necessary that some portion of the cannula be radiopaque.

However, the X-ray fluoroscopic image of the medical device, such as a catheter or a cannula, is a two dimensional image so that even if a distal end portion of the medical device is rotated along its longitudinal axis, or if the device itself is deviated toward or away from the plane of the fluoroscopic screen, the resultant X-ray fluoroscopic image is substantially the same as that obtained along the intended, i.e. correct, direction. The doctor may then mistakenly believe that the device is correctly directed.

With the advent of intravascular imaging devices such as angioscopy and intravascular ultrasound, it becomes important to know the orientation of the medical device within the vascular lumen. For example, FIG. 1 illustrates an arterial vascular lumen 10 having an interior periphery 12 on which is located a plaque 14. A medical device 20 having a distal end 22 is inserted into the vascular lumen. If one were to visualize the abnormal structure or plaque 14 as being located at the twelve o'clock position 24 of the medical device, one has no sure way of knowing where the 12 o'clock position is in relation to the planar radiograph shown in FIG. 1B. That is, the fluoroscope 30 has a flat screen 32. Therefore, the abnormal structure 14 may be at position A or at position B as seen by the planar radiograph or outside of the plane represented by the X-Y coordinate, i.e. at position C.

This becomes an important issue when one wants to direct specific therapy at the structure which therapy frequently requires a different device, for example, a directional atherectomy device or directed laser beams. The operator, therefore, has to guide this device to the position on the fluoroscopic image and then rotationally orient the device so that the twelve o'clock position of the device is pointed at the location C of the vessel. This task is complicated by the size of the devices in question. The total diameter of the medical device may be no more than 1 or 2 millimeters and the fluoroscopic resolution of most radiographic equipment is at best $\frac{1}{2}$ to 1 millimeter. Therefore, it is very difficult for a surgeon to correctly orient a medical device with the radiopaque markers available at present.

Accordingly, it has been considered desirable to develop a new and improved tubular device meant to be inserted into an object and imaged with an X-ray source which would overcome the foregoing difficulties and others while providing better and more advantageous overall results.

BRIEF SUMMARY OF THE INVENTION

In accordance with the present invention, a tubular device is provided which is meant to be inserted into an object and imaged with an X-ray source.

More particularly, the tubular device comprises a body having an outer circumference and including a distal end and a radiopaque marker located on the body adjacent the distal end thereof. The marker extends around the outer circumference of the body no more than 180°. The marker has a polygonal shape so as to be easily distinguished on an X-ray or fluoroscopic image of the body.

In accordance with another aspect of the present invention, a medical device is provided.

More particularly in accordance with this aspect of the invention, the device comprises a body having an outer circumference and including a distal end portion. A first radiopaque marker is located on the body adjacent the distal end portion. A second radiopaque marker is located on the body adjacent the distal end portion and spaced from the first radiopaque marker. Each of the first and second radiopaque markers extends no more than 90° around the circumference of the body.

In accordance with still another aspect of the present invention, an intravascular device is provided.

More particularly in accordance with this aspect of the invention, the intravascular device comprises a body having an outer periphery and including a distal end portion. A first substantially rectangular radiopaque marker is embedded in the outer periphery of the body adjacent the distal end portion such that it extends only partially around the outer periphery of the body. A second substantially rectangular radiopaque marker is embedded in the outer periphery of the body adjacent the distal end portion such that it extends only partially around the outer periphery of the body. The first radiopaque marker is spaced from the second radiopaque marker.

One advantage of the present invention is the provision of a new and improved tubular device meant to be inserted into an object and imaged with an X-ray source.

Another advantage of the present invention is the provision of a radiopaque marker system which can be placed in the wall of a tubular device and in which a fluoroscopic or X-ray film image of each rotational position of the marker is unique for the cardinal rotations, 0°, 90°, 180° and 270° of the tubular device.

Still another advantage of the present invention is the provision of a marker system which has maximum visibility in a fluoroscopic or X-ray film image.

Yet another advantage of the present invention is the provision of a marker system for a device such that the system includes distinct markers located in two adjacent quadrants with the markers being spaced from each other in a diagonal fashion.

A further advantage of the present invention is the provision of a marker system which is adapted for use in a medical environment where the total diameter of the medical device may be no more than one or two millimeters and wherein the radiopaque marker is still readily visible in a fluoroscopic or X-ray film image.

A still further advantage of the present invention is the provision of a marker system which can be used in a wide variety of medical devices such as a catheter, an angioscope, an intra-cardiac ultrasound device, a directional atherectomy device or a cannula.

A yet further advantage of the present invention is the provision of a marker system for any type of a tubular device that is intended to be placed in any type of body such that the position and rotational orientation of the tubular device within the body can be identified by X-rays.

Still other benefits and advantages of the invention will become apparent to those skilled in the art upon a reading and understanding of the following detailed specification.

BRIEF DESCRIPTION OF THE DRAWINGS

The invention may take physical form in certain parts and arrangements of parts preferred and alternate embodiments of which will be described in detail in this specification and illustrated in the accompanying drawings which form a part hereof and wherein:

FIG. 1A is a perspective view showing the state of a catheter distal end portion when a conventional catheter is inserted in a vascular lumen;

FIG. 1B is a view showing an X-ray fluoroscopic image of the catheter of FIG. 1A;

FIG. 2 is a perspective view of a device having a pair of distinct radiopaque markers according to a preferred embodiment of the present invention;

FIG. 3 is a cross-sectional view through a directional aetherectomy device that incorporates the preferred embodiment of the present invention;

FIG. 5 is a perspective view, partially cut away, of a directional laser device located within a vascular lumen;

FIG. 6A is a perspective view of a marker device according to an alternate embodiment of the present invention;

FIG. 6B is a developed view of the marker illustrated in FIG. 6A;

FIG. 7A is a developed view of a marker device according to another alternate embodiment of the present invention in a first rotational orientation; and FIG. 7B is a developed view of the marker of FIG. 7A in a second rotational orientation.

DETAILED DESCRIPTION OF THE PREFERRED AND ALTERNATE EMBODIMENTS

Figure 4:
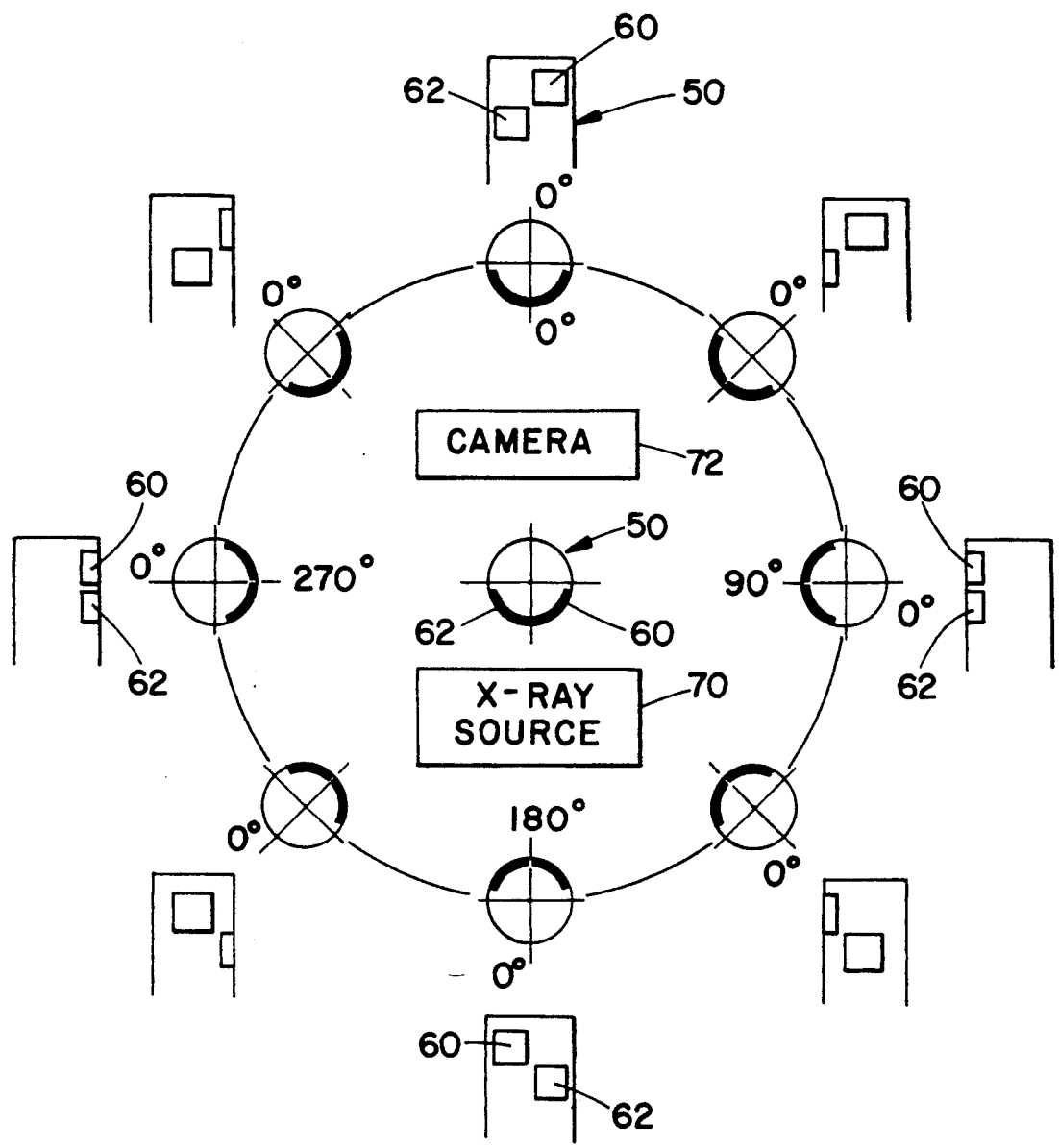
FIG. 4 is a series of views of an X-ray fluoroscopic image of the pair of radiopaque markers of the device of FIG. 2 when viewed from the rotational directions indicated.

Referring now to the drawings which are for purposes of illustrating the preferred and alternate embodiments of the present invention and not for limiting same, FIG. 2 illustrates the preferred embodiment of the marker device according to the present invention. While the marker device will be described in use in a medical environment, it should be appreciated that the device can also be utilized in an industrial environment or any other environment in which a tubular body needs to be inserted inside another body and the location of the tubular body as well as its rotational orientation within the other body needs to be imaged with X-rays such as on X-ray photographs or a fluoroscope.

Figure 8:
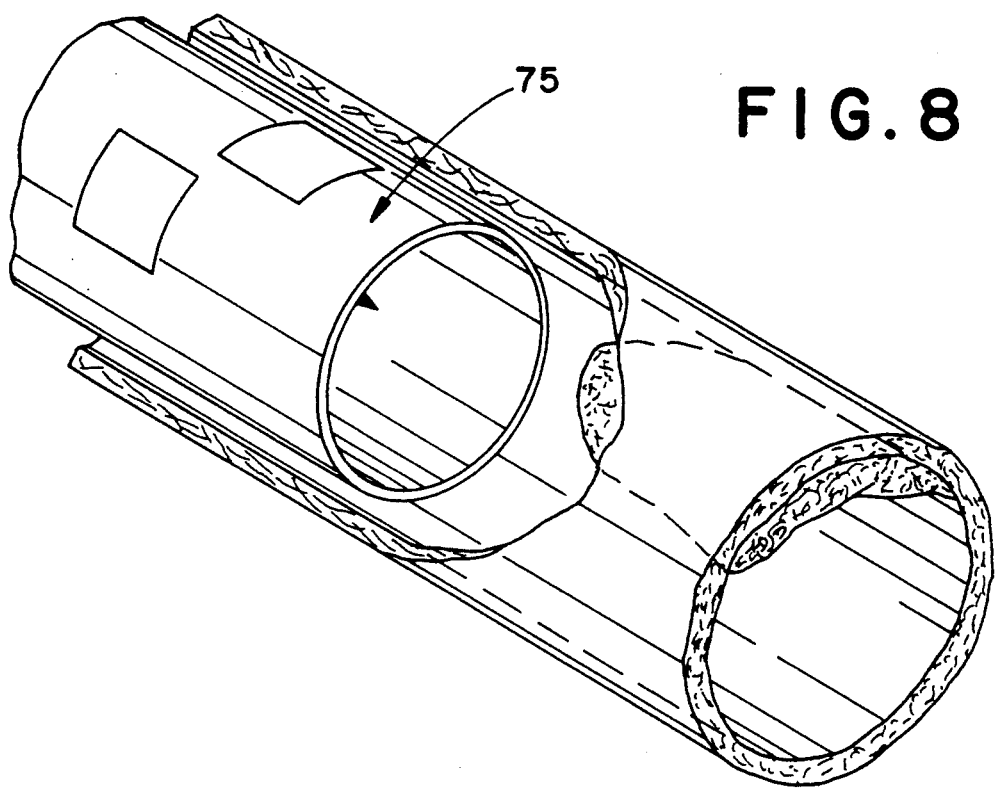
FIG. 8 is a perspective view of an angioscope inserted in a vascular lumen with the angioscope incorporating the preferred embodiment of the present invention; and, FIG. 9 is a perspective view of a directional atherectomy device incorporating the preferred embodiment of the present invention.
Figure 9:
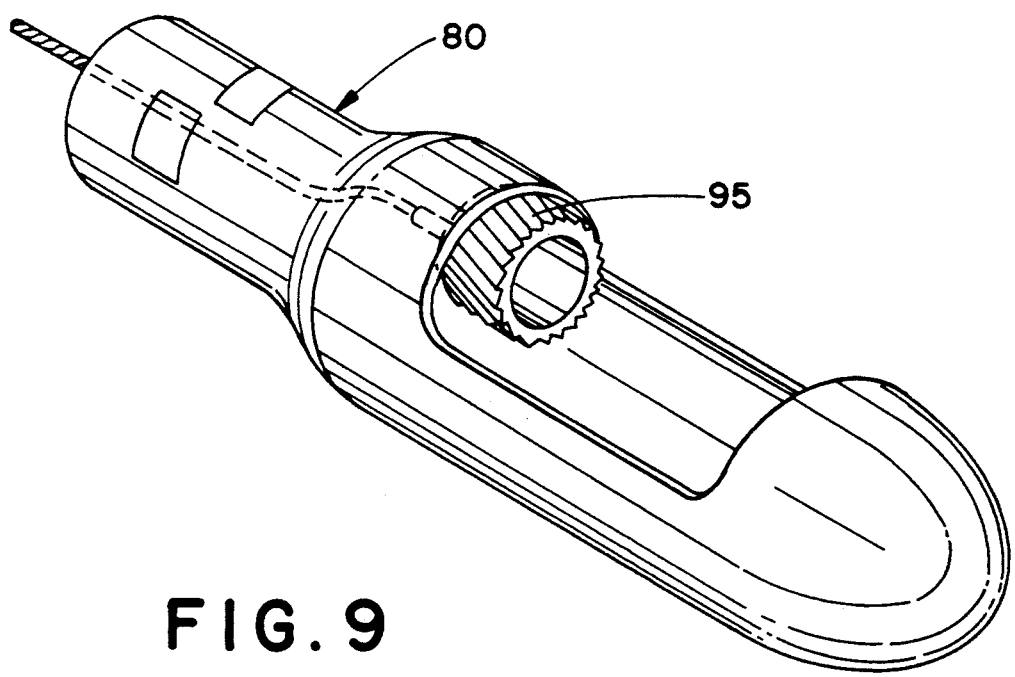

FIG. 2 illustrates a medical device in abstract which may be e.g. a catheter of any of the known types such as an angiographic catheter, a cardiac minute volume measuring catheter, a urethral catheter, a colangiographic catheter, a thoracic catheter or an angioplasty catheter. The medical device could also be a cannula such as an endotracheal tube, a tracheostomy tube or the like. Moreover, the medical device can be a directional atherectomy device, as shown in FIG. 9, an angioscope as shown in FIG. 8 or an intracardiac ultrasound device or the like all of these devices include a body 50 which is tubular in form as at 52 and has a distal end 54 and an outer periphery 56. Located on the outer periphery, or adjacent thereto, and near the distal end is a first marker 60 and a second marker 62. These markers can be so spaced from each other that they contact each other only at a point 64. In other words, the markers are diagonally spaced from each other. However, it should be appreciated that the markers could, if desired, contact each other along a common wall as shown in FIG. 6B. Alternatively, the markers could, if desired, be somewhat spaced from each other as in the embodiment of FIG. 4. In this embodiment, it is evident that the markers do not contact each other at all.

Preferably, the markers 60 and 62 are rectangular in shape. If desired, the markers can be precisely square in shape. While the body 50 is made from a suitable material which is transparent to X-rays, such as a plastic or the like, the radiopaque markers can be made from a suitable conventional metal or the like. One such metal which is deemed to be particularly advantageous in a medical setting is the metal gold. To this end, the markers 60 and 62 can comprise squares of gold foil or the like.

With reference now to FIG. 4, this figure illustrates the medical device of FIG. 2 within an X-ray viewing system. An X-ray source 70 transmits through the body 50, which is located in a suitable portion of the anatomy of a human or another animal (not illustrated for the sake of simplicity), and the X-ray image is picked up by a camera 72. As the device is rotated around its longitudinal axis, the rotational positions of the two markers 60 and 62 are shown for every 45° segment together with the views of the markers as seen by fluoroscopy. The fluoroscopic images are shown radially outside the circle of the various rotational orientations of the device. FIG. 4 clearly demonstrates that the marker positions are unique for each of the cardinal positions 0°, 90°, 180° and 270°. Intermediate positions from those illustrated can also be arrived at by a suitable rotation of the device so that the markers are as shown.

It is particularly noted that due to the diagonal placement of the two markers, the fluoroscopic view of the markers is different in the 0° versus the 180° rotational position of the device. That is, in the 0° position, the first marker 60 is located upward and to the right of the second marker 62. In contrast, in the 180° rotational position of the body 50, the first marker 60 is located upwards and to the left of the second marker 62. Therefore, the markers will present a different image on a fluoroscope or an X-ray film depending upon whether the body is at the 0° rotational position or the 180° rotational position. Similarly, it can be seen that the 90° and 270° rotational positions of the body 50 are different. More specifically, in the 90° position of the body 50, the markers 60 and 62 are located in the left hand half of the body 50. In contrast, in the 270° rotational position of the body 50, the markers 60 and 62 are located in the right hand half of the body 50. It is also evident that in the 45°, 135°, 225° and 315° rotational positions of the body 50 about its longitudinal axis, will present different and unique views on a fluoroscope or on X-ray film. Accordingly, the provision of two diagonally located markers will enable medical personnel to precisely identify the rotational orientation of the medical device within a body.

In clinical use, and with reference to FIG. 5, once a structure is located on a wall 76 of a vascular lumen 77 by an intravascular imaging device, such as an angioscope 75 illustrated in FIG. 8 to be at a twelve o'clock position which corresponds e.g. to position C in FIG. 1A of the drawings, a radiograph is taken of the device showing the precise orientation of the markers on the device. The imaging device can then be removed and replaced by a therapeutic device such as a directional laser treatment device 78 or a directional atherectomy device 80 illustrated in FIG. 9. When the therapeutic device is inserted, the physician may then guide the device to the desired location via fluoroscopy and rotationally orient the treatment face of the device to position C of the lumen (as in FIG. 1A) by duplicating the marker position of the previously taken radiograph. The markers of the laser treatment device 78 are not visible in FIG. 5. The rotational orientation of the markers on the angioscope 75 of FIG. 8 and the directional atherectomy device 80 of FIG. 9 can be seen to be the same. This orients the cutting edge of the directional atherectomy device so that it faces the plaque material illustrated on the artery of FIG. 8.

A major advantage of the instant system is that it is small enough to fit onto the conventional intravascular devices and yet large enough to be readily imaged by the conventional fluoroscopy devices present in medical offices and laboratories.

It is also an important advantage of the present invention that the marker system disclosed works well even when the medical device is out of the plane defined by the X-Y axis as in FIG. 1. In reality, the medical device is probably pointing slightly towards the X-ray source or the X-ray image tube and generally would not be exactly in the X-Y plane as illustrated. In that case, the length of the markers as seen fluoroscopically would simply have shortened and the gap between the two markers would also have shortened proportionally. The image obtained, however, will still allow a fair degree of accuracy in regard to the rotational orientation of the intravascular device.

With reference now to FIG. 3, the use of the marker system in a directional aetherectomy device will be illustrated. The device includes an elongated body 80 with an outer periphery 82 which has an indented portion 84. Located in the indented portion is a first marker 86 and a second marker 88. The cross-sectional view of FIG. 3 is along a line which intersects the lower edge of one marker and the upper edge of the other marker (as in, e.g., the lower edge of the marker 60 and upper edge of the marker 62 of FIG. 2). As is evident from FIG. 3, the markers together occupy somewhat less that a 180° segment of the 360° circumference of the body 80. Extending longitudinally within the body is a lumen 90. A passage 92 extends radially from the lumen to the outer periphery 82 of the body 80.

Extending longitudinally through the lumen 90 of the body 80 is a coil 94 which drives a directional blade or shaving device 95 at the distal end of the aetherectomy device as shown in FIG. 9. The cross-sectional view of FIG. 3 is proximal to the aetherectomy blade and, therefore, the blade is not visible in FIG. 3. Extending through port 92 is a wire 96 which is connected to the blade. The wire also extends longitudinally through the lumen 90 within the device 80 in a manner spaced from the coil 94. It is evident that the body 80 of the device is made from a suitable thermoplastic material which is transparent to X-rays. While the coil 94 and wire 96 are not transparent and will reflect X-rays, their reflection will be masked by the much greater reflection of the two markers 86 and 88.

The marker system will insure that the lumen or blood vessel is treated circumferentially by the directional aetherectomy device. For example, if the treatment delivered by the device is directed over an arc length of 45°, the device will have to be rotated seven times in one direction, each rotation covering 45°, after the device is initially positioned in the body, in order to cover the entire circumference of the vessel. Without the guidance of the marker system of the instant invention, the exact position of the treatment arc after each rotation could only be guessed at and inadequate or incomplete treatment could very easily result.

While in FIG. 3, the markers 86 and 88 are shown as being embedded in the outer periphery 82 of the catheter 80, it is evident that the markers could also be secured to the outer periphery 82 by adhesive or the like if that was considered desirable or necessary from either a functional or an economic standpoint.

As mentioned, the marker system is not limited to a medical field of use where one may need to know the radial orientation of a device within a tubular lumen such as a blood vessel, the urether or the intestine. Rather, the marker system can also be used in any radiographic imaging environment where a radial or rotational orientation needs to be derived from planar imaging.

Although the marker system illustrated in FIGS. 2–4 comprises a pair of diagonally spaced rectangular (and substantially square) markers, it is evident that other variations could also be provided. More specifically, although the two markers 60 and 62 in FIG. 4 of the drawings are shown as being located on either side of the 180° point of the circumference of the body 50, they could be located on either side of the 360° point of the body. It is evident that the periphery of the medical device 50 can be conceived of as having four quadrants. Each of the markers 60 and 62 is located in a respective one of the quadrants. The size of the markers can encompass an arc of somewhere between 45° to 90° within its respective quadrant. The actual size of the markers would obviously depend on the total diameter of the device and the relative radiopacity of the markers compared to that of the device and the visibility of the markers on the fluoroscopic screen.

With reference now to FIGS. 6A and 6B, conceptually the marker system of the preferred embodiment depends on marking two adjacent quadrants in a diagonal fashion. Therefore, rather than using a pair of diagonally spaced rectangles or squares 60 and 62 such as is illustrated in FIG. 2, one can provide a diamond shaped marker. More specifically, FIG. 6A illustrates a device 110 having an outer periphery 112 and a distal end 114. A diamond-shaped marker 120 is secured to the outer periphery 112. It is evident that the marker 120 is oriented at an angle to a longitudinal axis extending through the upper and lower tips of the diamond-shaped marker. The marker can either be adhesively secured to the outer periphery of the device or it could be embedded within the outer periphery in a suitable indentation therein as illustrated in the embodiment of FIG. 3.

With reference now to FIG. 6B, the diamond shaped marker 120 can also be conceived of as being composed of a pair of trapezoids 122 and 124 which abut each other along a line of contact 126 formed by their base lines. As with the embodiment illustrated in FIGS. 2–4, each rotational orientation of the device 110 will lead to a visually distinctive view of the marker 120. This enables the viewer of a fluoroscopic image or X-ray film to accurately determine the rotational orientation of the device 110 in the body into which it is inserted.

The shape of the individual markers is illustrated in FIGS. 2–4 as being rectangular, and preferably square. This is to maximize visibility for relatively small diameter medical devices such as catheters and the like. Other shapes may, however, be used for larger medical and other types of devices in order to fulfill the same function.

For example, one could provide a radiopaque marker 130 such as the letter E illustrated in FIG. 7A of the drawings. With this type of marker, the view of the marker at the 0° position of rotational orientation of the device to which the marker is attached would be a normal letter E. In contrast, as illustrated in FIG. 7B, the rotational orientation of the device at 180° would provide a fluoroscopic image of a backwards E. Other rotational orientations of the device would lead to yet other images on the fluorospic screen. Therefore, essentially each rotational orientation of the device to which the marker is attached would lead to a different and distinctive view of the marker thereby enabling the user to accurately assess the rotational orientation of the device to which the marker is attached.

The invention has been described with reference to preferred and alternate embodiments. It should be appreciated that alterations and modifications will occur to those of average skill in the art upon the understanding and appreciation of this specification. It is intended to include all such modifications and alterations which come within the scope of the appended claims and the equivalents thereof.

What is claimed is:

1. A medical device comprising:
    a body having an outer circumference and a distal end portion;
    a first radiopaque marker located on said body adjacent said distal end portion; and,
    a second radiopaque marker located on said body adjacent said distal end portion, and spaced from said first radiopaque marker, wherein each of said first and second radiopaque markers extends no more than 90 degrees around said circumference of said body wherein said first and second markers are so located in relationship to each other that they will present different images as the body is rotated around its longitudinal axis such that a rotational orientation of the device can be determined.

2. The medical device of claim 1 wherein said first marker is rectangular.

3. The medical device of claim 2 wherein said first marker is embedded in said body so that said outer circumference thereof is smooth.

4. The medical device of claim 1 wherein said second marker is rectangular.

5. The medical device of claim 4 wherein said second marker is embedded in said body so that said outer circumference thereof is smooth.

6. The medical device of claim 1 wherein said first and second markers contact each other only at a respective corner of each marker.

7. The medical device of claim 1 wherein the device comprises a directional laser device.

8. The medical device of claim 1 wherein the device comprises an angioscope.

9. The medical device of claim 1 wherein the device comprises a directional aetherectomy device.

10. A radiopaque marking system for a device meant to be inserted into an object and imaged with an X-ray source, comprising:
    a body having a distal end and an outer periphery which can be divided into four quadrants;
    a first radiopaque marker section comprising a discrete geometric figure located only in a first quadrant of said body adjacent said distal end; and, a second radiopaque marker section comprising a discrete geometric figure located only in a second quadrant of said body adjacent said distal end wherein said first and second marker sections present different images as the body is rotated around a longitudinal axis thereof to allow a rotational orientation of the body to be identified.

11. The marking system of claim 10 wherein said first and second quadrants of said outer periphery of said tube are located adjacent each other.

12. The marking system of claim 10 wherein said first and second radiopaque marker sections comprise rectangles.

13. The marking system of claim 12 wherein said first and second radiopaque sections comprise squares.

14. The marking system of claim 10 wherein said first and second radiopaque marker sections comprise two trapezoidal sections which share a common wall.

15. An intravascular device comprising:
a body having an outer periphery and including a distal end portion;
a first substantially polygonal radiopaque marker embedded in said outer periphery of said body adjacent said distal end portion and extending less than 180° around said outer periphery of said body; and,
a second substantially polygonal radiopaque marker embedded in said outer periphery of said body adjacent said distal end portion and extending less than 180° around said outer periphery of said body, wherein said first radiopaque marker is spaced from said second-radiopaque marker.

16. The intravascular device of claim 15 wherein said first marker is square.

17. The intravascular device of claim 15 wherein said second marker is square.

18. The intravascular device of claim 15 wherein the device comprises a directional laser device.

19. The intravascular device of claim 15 wherein the device comprises an angioscope.

20. The intravascular device of claim 15 wherein the device comprises a directional aetherectomy device.

21. A tubular device meant to be inserted into an object and imaged with an X-ray source, comprising:
a body having an outer circumference and including a distal end;
a radiopaque marker located on said body adjacent said distal end thereof, said marker extending around said outer circumference of said body less than 180 degrees, wherein said marker has a polygonal shape so as to be easily distinguished on an X-ray or fluoroscopic image of said body.

22. The device of claim 21 wherein said marker is embedded in said body.

23. The device of claim 21 wherein said marker comprises a diamond-shaped member.

24. The device of claim 21 wherein said marker comprises a pair of rectangular members which contact each other along at least one corner.

* * * * *